United States Patent [19]

Ong et al.

[11] Patent Number: 4,869,988
[45] Date of Patent: Sep. 26, 1989

[54] PHOTOCONDUCTIVE IMAGING MEMBERS WITH N,N-BIS(BIARYLYL)ANILINE, OR TRIS(BIARYLYL)AMINE CHARGE TRANSPORTING COMPONENTS

[75] Inventors: Beng S. Ong; Giuseppa Baranyi, both of Mississauga, Canada

[73] Assignee: Xerox Corporation, Stamford, Conn.

[21] Appl. No.: 274,159

[22] Filed: Nov. 21, 1988

[51] Int. Cl.⁴ ............................................. G03G 5/14
[52] U.S. Cl. ........................................................ 430/59
[58] Field of Search ........................................... 430/59

[56] References Cited

U.S. PATENT DOCUMENTS

| | | |
|---|---|---|
| 3,180,730 | 4/1965 | Klupfel et al. |
| 3,265,496 | 8/1966 | Fox. |
| 4,233,384 | 11/1980 | Turner et al. ........................ 430/59 |
| 4,273,846 | 6/1981 | Pai et al. ............................. 430/59 |
| 4,450,218 | 5/1984 | Takei et al. .......................... 430/59 |
| 4,471,039 | 9/1984 | Borsenberger et al. .............. 430/58 |
| 4,582,772 | 4/1986 | Teuscher et al. ..................... 430/58 |
| 4,637,971 | 1/1987 | Takei et al. .......................... 430/59 |
| 4,664,995 | 5/1987 | Horgan et al. ....................... 430/59 |
| 4,719,163 | 1/1988 | Staudenmayer et al. ............. 430/58 |
| 4,725,518 | 2/1988 | Carmichael et al. ................. 430/58 |
| 4,769,302 | 9/1988 | Ueda .................................... 430/59 |

FOREIGN PATENT DOCUMENTS 5800284 9/1981 Japan.
0132953 3/1986 Japan.

Primary Examiner—Roland E. Martin
Attorney, Agent, or Firm—E. O. Palazzo

[57] ABSTRACT

A photoconductive imaging member comprised of a supporting substrate, an inorganic photogenerating layer, or a photogenerating layer comprised of metal free phthalocyanines, metal phthalocyanines, vanadyl phthalocyanines, squaraines, perylenes, or dibromoanthrone; and a charge transport layer comprised of N,N-bis(biarylyl)aniline compounds of Formula (I) or tris(biarylyl)amine compounds of Formula (II), wherein R, R', R" are independently selected from the group consisting of hydrogen, halogen, alkyl, aryl, alkoxy, and alkoxycarbonyl, and x, y, and z are the numbers 0, 1, or 2. Examples of charge transport compounds include N,N-bis(4-biphenylyl)-3,5-dimethoxyaniline (Ia); N,N-bis(4-biphenylyl)-3,5-dimethylaniline (Ib); N,N-bis(4-methyl-4'-biphenylyl)-3-methoxyaniline (Ic); N,N-bis(4-methyl-4'-biphenylyl)-3-chloroaniline (Id); N,N-bis(4-bromo-4'-biphenylyl)-3,5-dimethoxyaniline (Ig); 4-biphenylyl bis(4-ethoxycarbonyl-4'-biphenylyl)amine (IIa); 4-biphenylyl bis(4-acetoxymethyl-4'-biphenylyl)amine (IIb); or 4-ethoxycarbonyl-4'-biphenylyl bis(4-methyl-4'-biphenylyl)amine(IId).

44 Claims, 1 Drawing Sheet

PHOTOCONDUCTIVE IMAGING MEMBERS WITH N,N-BIS(BIARYLYL)ANILINE, OR TRIS(BIARYLYL)AMINE CHARGE TRANSPORTING COMPONENTS

BACKGROUND OF THE INVENTION

This invention is generally directed to photoconductive imaging members with certain charge transport components. More specifically, the present invention is directed to layered imaging members with charge transport components containing N,N-bis(biarylyl)aniline and tris(biarylyl)amine derivatives. The aforementioned charge transport components possess a number of advantages including excellent compatibility with resinous binders, such as polycarbonates and polyesters, thereby suppressing or substantially eliminating the undesirable crystallization of these components in the transport layers. Additionally, the charge transport compounds illustrated herein enable photoconductive imaging members that can be selected for electrophotographic imaging and printing processes for an extended number of imaging cycles exceeding, for example, 50,000 cycles. Also, imaging members with the charge transport compounds of the present invention possess excellent high photosensitivity, and possess other advantages, thus enabling, for example, the selection of these members in high speed imaging and printing devices. Furthermore, the imaging members of the present invention exhibit relatively low or negligible dark decay characteristics, thereby permitting the generation of high quality images for imaging and printing applications. In one embodiment of the present invention, the imaging member is comprised of a supporting substrate, a photogenerating layer, and in contact therewith a charge transport layer comprised of N,N-bis(biarylyl)aniline or tris(biarylyl)amine derivatives illustrated herein. The charge or hole transport layer can be located as the top layer of the imaging member, or alternatively it may be situated between the supporting substrate and the photogenerating layer.

The formation and development of electrostatic latent images on the imaging surfaces of photoconductive materials by electrostatic means is well known. Numerous different photoconductive members for use in xerography are known such as selenium, alloys of selenium, layered imaging members comprised of arylamine charge transport layers, reference U.S. Pat. Nos. 4,265,990 and 4,273,846, and imaging members with charge transport layers comprised of polysilylenes, reference U.S. Pat. No. 4,618,551. Nevertheless, layered photoresponsive imaging members with the transport molecules N,N-bis(biarylyl)aniline or tris(biarylyl)amine derivatives of the present invention are equal to or superior to other photoresponsive imaging devices in terms of device long-term stability, device performance, sensitivity to changes in environmental conditions, costs of materials and device fabrication.

There are also known photoreceptor materials comprised of inorganic or organic materials wherein the charge carrier generation and charge carrier transport functions are accomplished by discrete contiguous layers. Additionally, photoreceptor materials are disclosed in the prior art which include an overcoating layer of an electrically insulating polymeric material, and in conjunction with this overcoated type photoreceptor there have been proposed a number of imaging methods.

Specifically, layered photoresponsive devices, including those comprised of generating layers and transport layers, are disclosed in U.S. Pat. No. 4,265,990, and overcoated photoresponsive materials containing a hole injecting layer overcoated with a transport layer, followed by an overcoating of a photogenerating layer and a top coating of an insulating organic resin, reference U.S. Pat. No. 4,251,612. Examples of generating layers disclosed in these patents include trigonal selenium and vanadyl phthalocyanine, while examples of the transport layer that may be employed are comprised of aryldiamines as mentioned therein. The '990 patent is of particular interest in that it discloses layered photoresponsive imaging members similar to those illustrated in the present application with the exception that the charge transporting component of the members of the present invention are comprised of, for example, tris(biarylyl)amine or N,N-bis(biarylyl)aniline compounds. These members can be utilized in electrophotographic methods by, for example, initially charging the member with an electrostatic charge and imagewise exposing to form an electrostatic latent image which can be subsequently developed to form a visible image.

As a result of a patentability search, there were located Japanese Koni abstract J5 8002-849 which discloses a photoconductors comprising a laminate of a carrier generation layer A, and a charge transport layer B which layer contains an amine derivative of Formula I, which amine is similar in some instances to the charge transport compounds of the present invention, a carbazole deriviative of Formula II, and a polymeric organic semiconductor having a condensed aromatic ring or hetero ring in the side chain; Ricoh Japanese abstract 61-132953 which discloses an electrophotographic sensitive body with a trisazo pigment of Formula I, and a charge transfer layer of Formula V, which transfer layer is similar in some instances to the charge transport compounds of the present invention; and as background or collateral interest U.S. Pat. Nos. 4,233,384; 4,273,846; 4,450,218; 4,637,971 and 4,719,963.

Illustrated in related copending application U.S. Ser. No. (not yet assigned,) with the listed inventors Beng Ong, Barkev Keoshkerian, and Giuseppa Baranyi, entitled Photoconductive Imaging Members With Diaryl Biarylamine Charge Transporting Components, the disclosure of which is totally incorporated herein by reference, are layered photoconductive imaging members comprised of a supporting substrate, a photogenerating layer comprised of inorganic, photoconductive pigments, optionally dispersed in an inactive resinous binder, and in contact therewith a charge transport layer comprised of diphenylbiphenylamines of Formula (I) dispersed in resinous binders.

In Belgium Pat. No. 763,540, there is disclosed an electrophotographic member having at least two electrically operative layers, the first layer comprising a photoconductive layer which is capable of photogenerating charge carriers, and injecting the photogenerated hole into a continuous active layer containing a transport organic material which is substantially non-absorbing in the spectral region of intended use, but which is active and that allows injection of photogenerating holes from the photoconductive layer and allows these holes to be transported through the active layer. The active polymers may be mixed with inactive polymers or nonpolymeric materials.

Also, there is illustrated in U.S. Pat. Nos. 4,232,102 and 4,233,383, the disclosures of which are totally incorporated herein by reference, the use of sodium carbonate doped and barium carbonate doped photoresponsive imaging members containing trigonal selenium. Other representative patents disclosing layered photoresponsive devices include U.S. Pat. Nos. 4,115,116; 4,047,949 and 4,081,274.

While imaging members with various charge transporting substances, including some aryl amines, are suitable for their intended purposes there continues to be a need for improved members, particular layered members, which are comprised of hole transporting substances with certain advantages. Further, there continues to be a need for layered imaging members wherein the layers are sufficiently adhered to one another to allow the continuous use of such members in repetitive imaging systems. Also, there continues to be a need for charge transporting substances which are compatible with various resinous binders, such as polycarbonates, thereby ensuring the long-term stability of the photoconductive imaging devices within which they are incorporated. Also, there continues to be a need for charge transporting substances that are also useful as protective overcoating materials, and as interface materials for various imaging members. Furthermore, there is a need for charge transport compounds that are nontoxic, and are inert to the users of the devices, or imaging members within which they are incorporated. A further need resides in the provision of efficient charge transport compounds which are readily accessible synthetically from economical commercial starting materials. Another need resides in the provision of layered photoconductive imaging and printing devices that possess high photosensitives, and thus are useful for high speed imaging and printing applications.

SUMMARY OF THE INVENTION

It is therefore an object of the present invention to provide layered photoresponsive imaging members with many of the advantages indicated herein.

It is another object of the present invention to provide improved layered photoresponsive imaging members with certain charge transporting layer components dispersed in an inactive resinous binder in contact with a photogenerating layer.

In a further object of the present invention there is provided an improved layered photoresponsive imaging member with a photogenerating layer situated between a supporting substrate, and a charge transport layer comprised of the components disclosed hereinafter.

In yet another object of the present invention there is provided an improved photoresponsive imaging member comprised of a charge transport layer situated between a supporting substrate, and an inorganic photogenerating layer.

In yet another object of the present invention there are provided imaging and printing methods with the layered imaging members disclosed herein.

Another object of the present invention resides in the provision of charge transport compounds which are non-toxic and inert to the users of the devices within which they are incorporated.

A further object of the present invention is to provide improved layered imaging members containing charge transport compounds described herein, and which members are insensitive to changes in environmental conditions, including relative humidities of from about 20 to about 80 percent.

In yet a further object of the present invention there are provided novel efficient charge transport compounds which are readily accessible by simple common synthetic processes.

These and other objects of the present invention are accomplished by the provision of layered imaging members comprised of a photogenerating layer, and a charge transport layer comprised of certain N,N-bis(biarylyl)aniline or tris(biarylyl)amine derivatives of compounds. More specifically, the present invention is directed to layered imaging members comprised of inorganic photogenerating layers, and certain organic photogenerating components and in contact therewith charge transport layers comprised of tris(biarylyl)amine compounds, N,N-bis(biarylyl)aniline compounds, or mixtures thereof, derivatives dispersed in resinous binders, and wherein the charge transporting compounds are preferably present in an amount of from about 10 weight percent to about 95 percent by weight, and preferably from about 30 to about 60 percent by weight.

In one specific embodiment, the present invention is directed to an improved layered photoconductive imaging member comprised of a supporting substrate, a photogenerating layer comprised of inorganic, or certain organic photoconductive pigments, optionally dispersed in an inactive resinous binder, and in contact therewith a charge transport layer comprised of bis(-biarylyl)aniline derivatives (I), tris(biarylyl)amine derivatives (II) of the following formulas or mixtures thereof dispersed in resinous binders.

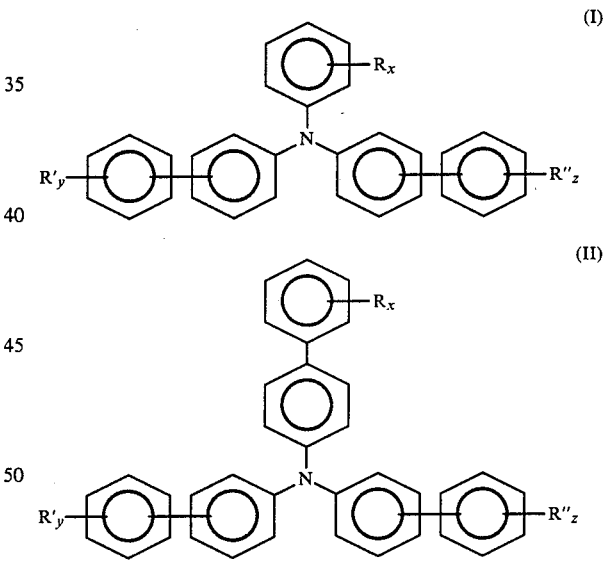

where R, R', R" are independently selected from the group consisting of hydrogen, halogen, includinb bromide, chloride, iodide, fluoride, alkyl, aryl, alkoxy, alkoxycarbonyl groups; x, y and z are the integers, or numbers 0, 1, or 2.

Examples of specific charge transporting components include N,N-bis(4-biphenylyl)-3,5-dimethoxyaniline (Ia); N,N-bis(4-biphenylyl)-3,5-dimethylaniline (Ib); N,N-bis(4-methyl-4'-biphenylyl)-3-methoxyaniline (Ic); N,N-bis(4-methyl-4'-biphenylyl)-3-chloroaniline (Id); N,N-bis(4-methyl-4'-biphenylyl)-4-ethylaniline (Ie); N,N-bis(4-chloro-4'-biphenylyl)-3-methylaniline (If); N,N-bis(4-bromo-4'-biphenylyl)-3,5-dimethoxyaniline (Ig); 4-biphenylyl bis(4-ethoxycarbonyl-4'-biphenylyl- )amine (IIa); 4-biphenylyl bis(4-acetoxymethyl-4'-biphenylyl)amine (IIb); 3-biphenylyl bis(4-methyl-4'-biphenylyl)amine (IIc); 4-ethoxycarbonyl-4'-biphenylyl bis(4-methyl-4'-biphenylyl)amine (IId); and the like, of the following formulas.

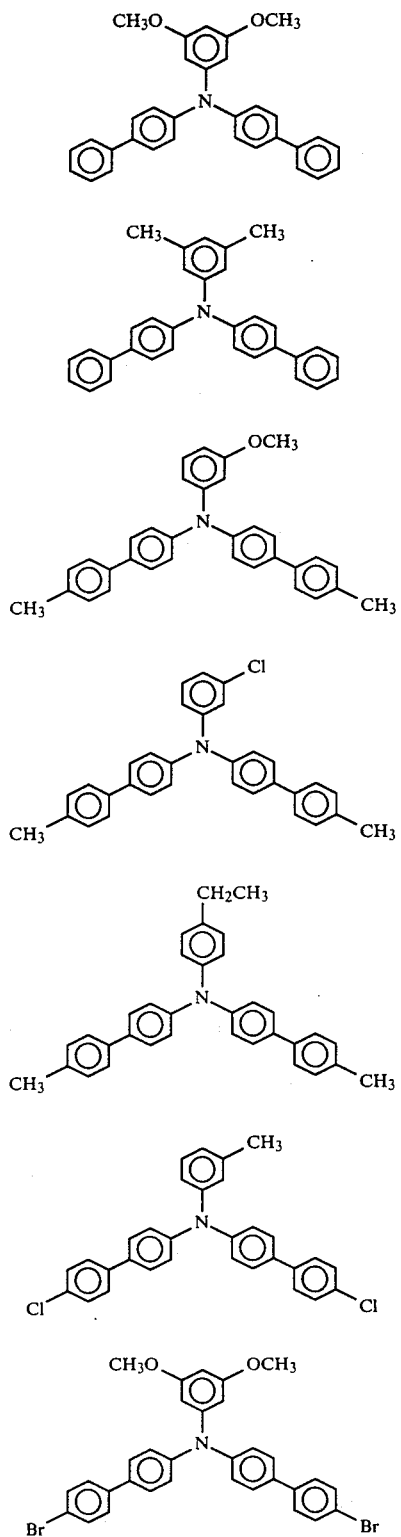

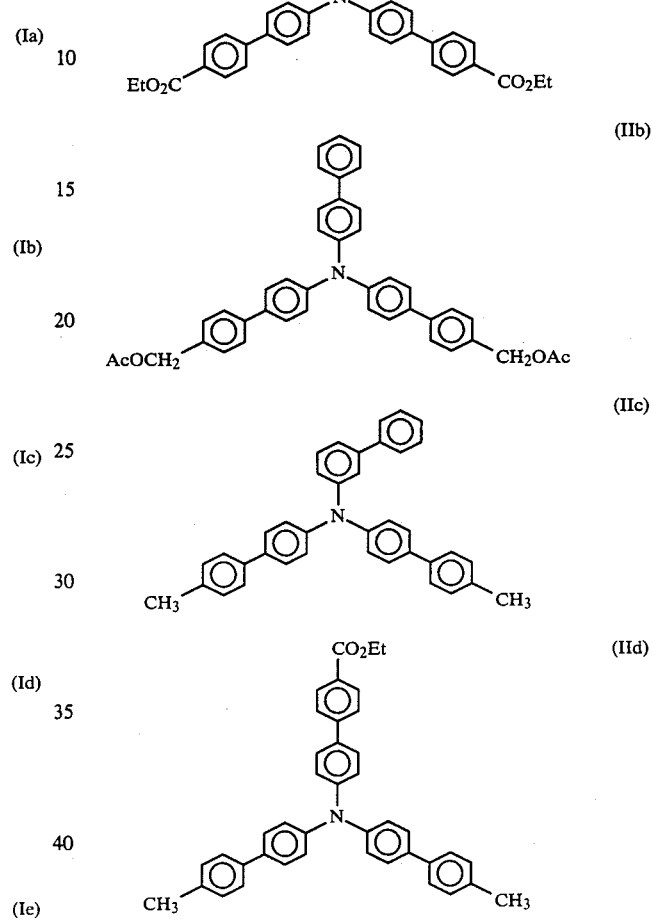

Aryl groups which may be substituted with alkyl, alkoxy, and other substituents include those with from about 6 to about 24 carbon atoms such as phenyl, naphthyl, and the like.

Examples of alkyl groups include those with from 1 carbon atom to about 25 carbon atoms, and preferably from about 1 carbon atom to about 8 carbon atoms, inclusive of methyl, ethyl, propyl, butyl, pentyl, hexyl, octyl, nonyl, decyl, pentadecyl, stearyl, and other similar substituents. Specific preferred alkyl groups are methyl, ethyl, propyl, and butyl.

Examples of alkoxy groups include those with from 1 carbon atom to about 10 carbon atoms, such as methoxy, ethoxy, propoxy, butoxy, pentoxy, and other similar substituents. Examples of alkoxycarbonyl groups include methoxycarbonyl, ethoxycarbonyl, isopropoxycarbonyl, n-propoxycarbonyl, butoxycarbonyl, pentoxycarbonyl, and the like.

The improved photoresponsive imaging members of the present invention can be prepared by a number of known methods, the process parameters and the order of the coating of the layers being dependent on the member desired. Thus, for example, the improved photoresponsive members of the present invention can be prepared by providing a conductive substrate with an optional hole blocking layer and optional adhesive layer, and applying thereto an inorganic photogenerating layer, and overcoating thereto a transport layer of N,N-bis(biarylyl)aniline or tris(biarylyl)amine derivatives of the present invention dispersed in an optional resinous binder. The improved photoresponsive imaging members of the present invention can be fabricated by common coating techniques such as by dip coating, draw-down coating, or by spray coating process, depending largely on the type of imaging devices desired. Each coating, however, is dried in a convection or forced air oven at a suitable temperature before the subsequent layer is applied thereto.

BRIEF DESCRIPTION OF THE DRAWINGS

For a better understanding of the present invention and further features thereof, reference is made to the following detailed description of various preferred embodiments wherein.

DETAILED DESCRIPTION OF THE INVENTION

Figure 1:
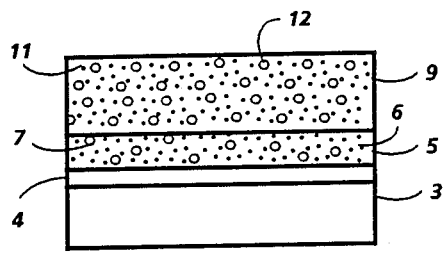
FIG. 1 represents a partially schematic cross-sectional view of a preferred photoresponsive imaging member of the present invention.

Illustrated in FIG. 1 is the improved photoresponsive imaging member of the present invention comprising a supporting substrate 3 of a thickness of from about 50 microns to about 5,000 microns, an optional charge blocking layer 4 of a thickness of from about 0.001 micron to about 0.1 micron, a charge carrier photogenerating layer 5 of a thickness of from about 0.1 micron to about 5 microns comprised of an inorganic photogenerating pigment 6, optionally dispersed in inactive resinous binder composition 7, and from about a 5 micron to about a 60 micron thick hole transport layer 9 comprised of the N,N-bis(biarylyl)aniline or tris(biarylyl)amine compounds of the formulas as illustrated herein as a charge transporting substance 11 dispersed in an inactive resinous binder 12. The aforementioned charge transport compounds can be present in an amount of from about 10 to about 75 percent by weight. In an alternative embodiment of the present invention, and in further regard to FIG. 1, the hole transporting layer can be situated between the supporting substrate and the photogenerating layer.

Figure 2:
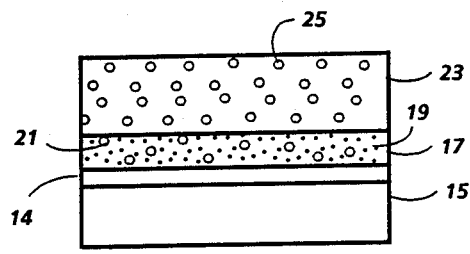
FIG. 2 represents a partially schematic cross-sectional view of a preferred photoresponsive imaging member of the present invention.

Illustrated in FIG. 2 is a preferred photoresponsive imaging member of the present invention comprised of a conductive supporting substrate 15 of aluminized Mylar of a thickness of about 50 microns, a charge blocking layer 14, a photogenerating layer 17 comprised of a trigonal selenium photogenerating pigment 19 optionally dispersed in a poly(vinylcarbazole) resinous binder 21 in the amount of from about 10 to about 60 percent by weight, and a charge transport layer 23 comprised of from about 30 to about 60 percent by weight of N,N-bis(biphenylyl)-3,5-dimethoxyaniline dispersed in a polycarbonate resinous binder 25.

The supporting substrate layers may be opaque or substantially transparent and may comprise any suitable material having the requisite mechanical properties. The substrate may comprise a layer of nonconductive organic or inorganic material having a conductive surface layer arranged thereon or a conductive material such as, for example, aluminum, chromium, nickel, indium, tin oxide, brass or the like. The substrate may be flexible or rigid, and many have any of many different configurations such as, for example, a plate, a cylindrical drum, a scroll and the like. The thickness of the substrate layer is generally from about 50 microns to about 5,000 microns.

Examples of photogenerating layers include those comprised preferably of inorganic photoconductive charge carrier generating materials, such as amorphous selenium alloys, halogen doped amorphous selenium, halogen doped amorphous selenium alloys, trigonal selenium, mixtures of Groups IA and IIA, elements, selenite and carbonates with trigonal selenium, reference U.S. Pat. Nos. 4,232,102 and 4,233,283, the disclosures of each of these patents being totally incorporated herein by reference, copper, and chlorine doped cadmium sulfide, cadmium selenide and cadmium sulfur selenide, and the like. Also, organic photogenerators, such as squaraines, perylenes, metal free phthalocyanines, metal phthalocyanines, vanadyl phthalocyanines, dibromoanthrone, and the like may be selected providing the objectives of the present invention are achieved. The aforementioned imaging members with the organic photogenerators indicated possess high photosensitivities, and excellent dark decay properties as compared to, for example, similar imaging members with trisazo photogenerating pigments. The thickness of this photogenerating layer is from about 0.1 micron to about 5 microns, and preferably from about 0.2 micron to about 2 microns in thickness depending on the loading of the photoconductive materials, which may vary from 5 percent to 100 percent by weight. Generally, it is desirable to provide this layer in a thickness which is sufficient to absorb about 90 percent or more of the incident radiation which is directed upon it in the imagewise exposure step. The maximum thickness of this layer is dependent primarily upon facts such as mechanical considerations, for example, whether a flexible photoresponsive device is desired. Optional resin binders for the photogenerating compositions are, for example, the polymers as illustrated in U.S. Pat. No. 3,121,006, the disclosure of which is totally incorporated herein by reference, polyesters, poly(vinylbutyrals), polycarbonate resins, epoxy resins, poly(hydroxyether) resins, and the like.

The transport layer also includes therein a highly insulating and transparent resinous material or inactive binder resinous material such as those described in U.S. Pat. No. 3,121,006, the disclosure of which is totally incorporated herein by reference. For the transport layer, a dispersion of, for example, from about 10 percent to 75 percent by weight of the charge transport compounds illustrated herein in an inactive resinous binder such as polycarbonate, especially Makrolon, and Merelom, polyester, epoxy resins, or the like is employed. The thickness of the transport layer is from about 5 microns to about 50 microns, the exact thickness depending predominantly on the nature of the intended applications. In addition, a layer of adhesive material to promote the adhesion of the transport layer to the photogenerating layer may be utilized. This layer may be comprised of common adhesive materials such as a polyester resin, especially 49,000 polyester available from Goodyear Chemical Company, acrylic polymers, and the like. A thickness of from about 0.001 micron to about 0.5 micron for this layer is generally employed. Hole blocking layers such as those derived from the polycondensation of aminopropyl trialkoxysilane or aminobutyl trialkoxysilane may optionally be introduced between the substrate and the photogenerating layer to suppress the dark decay characteristics of the imaging member. Typically, this layer has a thickness of from about 0.001 micron to about 5 microns or more in thickness, depending on the effectiveness with which this layer prevents the dark injection of charge carriers into the photogenerating layer.

The hole transporting N,N-bis(biarylyl)aniline and tris(biarylyl)amine compounds of the present invention are not commercially available; they can, however, by synthesized from readily available commercial reactant materials. There are many viable synthetic processes that can be utilized in the synthesis of these compounds, including the one step Ullman condensation of an aryl amine with an iodoarene. Thus, one process embodiment involves the condensation of a primary aryl amine or a primary biarylylamine with 2 equivalents of iodobiaryl, and another involves the condensation of a bis(biarylyl)amine with an iodoarene or iodobiaryl. The aforementioned Ullman condensation is generally accomplished in a suitable solvent such as a high-boiling hydrocarbon, including for example Soltrol 220, Soltrol 170, and the like, dimethylsulfoxide, dimethylformamide, dimethylacetamide, and the like, at temperatures of from ambient temperature to about 300° C., and preferably from 150° C. to 250° C. The condensation is executed in the presence of a catalyst and, for example, an alkali hydroxide base, and is generally completed within a period ranging from about 2 to about 48 hours. Preferred catalysts are copper powder, copper bronze powder, cuprous oxide, cuprous halides, cuprous triflate, and other suitable cuprous salts. The catalyst is employed in the amount of 0.1 to about 1.0 equivalent relative to the amount of iodoarene reactant usually selected with the preferred catalyst stoichiometry being in the order of about 0.5 equivalent of the iodoarene. Preferred bases are potassium hydroxide, potassium carbonate and selected aromatic amine bases such as, for example, pyridine and quinoline. The base is employed in about 10 percent to 100 percent excess to the iodoarene reactant, preferred stoichiometry being in the order of 50 percent excess in quantity. The products are generally isolated from the reaction mixture by usual work-up procedure, followed by column chromatography. They can be further purified by recrystallization. They are characterized by spectroscopic means and by elemental analysis.

The bis(biarylyl)aniline and tris(biarylyl)amine charge transport compounds of the present invention possess efficient hole transport properties and low dark conductivity characteristics. They are compatible with many common matrix binders ensuring their long-term stability in the transport layer. As the transport layer of the present invention is transparent to the visible light, all the visible radiations used in the exposure reaches the photogenerating layer without noticeable loss.

The following examples are being supplied to further define specific embodiments of the present invention, it being noted that these examples are intended to illustrate and not limit the scope of the present invention. Parts and percentages are by weight unless otherwise indicated.

EXAMPLE I

N,N-Bis(biphenylyl)-3,5-dimethoxyaniline(Ia):

A mixture of 28.0 grams of 4-iodobiphenyl, 4.1 grams of copper bronze powder, and 20.0 grams of potassium carbonate in 100 milliliters of Soltrol 220 was mechanically stirred in a round-bottomed flask under a nitrogen atmosphere. The mixture was heated with a heating mantle, and when the temperature reached 150° C., 7.65 grams of 3,5-dimethoxyaniline was added. The reaction mixture was subsequently heated under reflux at 220° C., and the progress of the reaction was monitored by thin layer chromatography. After five hours, the reaction mixture was filtered, and the filtrate was evaporated under reduced pressure to remove Soltrol 220. Purification of the brown residue by column chromatography on silica gel using a mixture of hexane and tetrahydrofuran (1:9) as the eluent afforded a light yellow solid which was recrystallized from isopropanol to afford 11.5 grams of the pure product N,N-bis(biphenylyl)-3,5-dimethoxyaniline, melting point 79° to 80° C.

$^1$H NMR (CDCl3), δ (ppm): 3.7(s, 6H); 6.2(t, $J_m$=2.0 Hz; 1H); 6.35(d, $J_m$=2.0 Hz; 2H); 7.1 to 7.7(m, 18H)

Elemental Analysis, Calcd. for $C_{32}H_{27}NO_2$: C, 84.00; H, 5.95; N, 3.06. Found: C, 84.11; H, 5.73; N, 3.24.

EXAMPLE II

Bis(4-ethoxycarbonyl-4'-biphenylyl)-4-biphenylylamine (IIa)

Seventeen (17) grams of iodine and 15 grams of ammonium persulfate were dissolved in a mixture of 10 milliliters of concentrated sulfuric acid, 225 milliliters of glacial acetic acid and 70 milliliters of water by stirring in a 1-liter round-bottomed flask. To the resulting solution was added 22.0 grams of 4-biphenylacarboxylic acid, and the mixture was heated at 80° C. with constant stirring for 2 hours. After addition of another 5 grams of ammonium persulfate, the reaction waas continued for another 10 hours. The hot reaction mixture was filtered, and the solid product was washed three times with water, and dried in vacuo at 80° C. for 24 hours, affording 34.7 grams of pure 4-iodo-4'-biphenylcarboxylic acid, melting point 303° to 305° C.

A suspension of 33.0 grams of 4-iodo-4'-biphenylcarboxylic acid in 300 milliliters of absolute ethanol and 400 milliliters of toluene was heated under reflux in a 2-liter flask in the presence of 0.5 milliliter of concentrated sulfuric acid. After 12 hours of heating, 300 milliliters of the solvent (toluene and ethanol) was gradually removed over a period of 5 hours by means of a Dean Stark apparatus. One hundred (100) milliliters each of absolute ethanol and toluene were then added, and the reaction was continued for another 12 hours. The reaction mixture was evaporated under reduced pressure to remove ethanol and toluene in the presence of 2 grams of sodium bicarbonate. The resulting solid residue was dissolved in methylene chloride, and washed several times with dilute aqueous sodium bicarbonate solution. The methylene chloride solution was dried with anhydrous magnesium sulfate, filtered, and evaporated to dryness to afford the crude product; the latter was recrystallized from hexane to provide 27.8 grams of pure ethyl 4-iodo-4-biphenylcarboxylate, melting point 105° to 106° C.

A suspension of 15.1 grams of the above prepared ethyl 4-iodo-4'-biphenylcarboxylate, 1.65 gram of copper bronze powder, and 8.0 grams of potassium carbonate in 50 milliliters of Soltrol 220 was mechanically stirred and heated under a nitrogen atmosphere. When the temperature reached 100° C., 3.62 grams of 4-aminobilhenyl was added. Subsequently, the reaction mixture was heated under reflux at 220° C., and the progress of reaction was monitored by thin layer chromatography. After 8 hours of reaction, another batch of 2.6 grams of potassium carbonate and 0.53 gram of copper bronze powder was added. The reaction was then continued for another 8 hours. The hot reaction mixture was then filtered, and the filtrate was evaporated under reduced pressure to provide a solid residue which was purified by column chromatography on silica gel using methylene chloride and hexane (1:1) as the eluent. Recrytallization from methylene chloride yielded 8.1 grams of the desired pure product bis(4-ethoxy carbonyl-4'-biphenylyl)-4-biphenylylamine, melting point of 200° to 201° C.

$^1$H NMR (CDCl$_3$), δ (ppm): 1.40(t, 6H); 4.40(q, 4H); 7.20 to 8.20(m, 25H).

Elemental Analysis, Calcd. for $C_{42}H_{35}NO_4$: C, 81.66; H, 5.71; N, 2.27. Found: C, 81.35; H, 5.91; N, 2.30.

EXAMPLE III

Bis[4-(acetoxymethyl)-4'-biphenylyl]-4-biphenylylamine (IIb)

A solution of 4.0 grams of bis(4-ethoxycarbonyl-4'-biphenylyl)-4-biphenylylamine (IIa) as obtained in Example II, and 40 milliliters of tetrahydrofuran was magnetically stirred in a 100-milliliter round-bottomed flask at room temperature. To this solution was added in small portions 0.26 gram of lithium aluminum hydride powder. After 1 hour of reaction, another 0.05 gram of lithium aluminum hydride was added. The reaction was continued for another hour before 5 milliliters of 10 percent aqueous sodium hydroxide solution and 2 grams of Celite powder were added. The reaction mixture was filtered, and the filtrate was evaporated to dryness. The residue was dissolved in 50 milliliters of methylene chloride, and washed twice with 5 percent aqueous sodium hydroxide solution, and twice with water. The methylene chloride solution was dried, filtered, and evaporated to give a white solid product. The latter bis(4-hydroxymethyl-4'-biphenylyl)-4-biphenylylamine was dried in vacuo at 80° C. for 24 hours, and used in the subsequent reaction without further purification. The yield was 3.5 grams.

A mixture of 3.5 grams of bis(4-hydroxymethyl-4'-biphenylyl)-4-biphenylyl-amine as obtained above, and 3.5 grams of triethylamine in 30 milliliters of methylene chloride was stirred in a 50-milliliter round-bottomed flask under a nitrogen atmosphere. To this mixture was added dropwise a solution of 1.0 gram of acetyl chloride in 2 milliliters of methylene chloride over a period of 5 minutes. After the addition, the mixture was stirred at room temperature for 2 hours. The reaction mixture was washed several times with water to remove the triethyl ammonium salt, dried with anhydrous magnesium sulfate, filtered, and evaporated to give the crude off-white product. Purification by treatment with decolorizing charcoal in isopropanol, followed by recrystallization from the same solvent afforded 2.9 grams of pure bis[4-(acetoxymethyl)-4'-biphenylyl]-4-biphenylylamine, 166° to 167.5° C.

$^1$H NMR (CDCl$_3$), δ (ppm): 2.15(s, 6H); 5.15(s, 4H); 7.15 to 7.70(m, 25H).

Elemental Analysis, Calcd. for $C_{42}H_{35}NO_4$: C, 81.66; H, 5.71; N, 2.27. Found: C, 81.73; H, 5.78; N, 2.17.

EXAMPLE IV

A layered photoresponsive imaging member with a transport layer comprised of a dispersion of N,N-bis(4-biphenylyl)-3,5-dimethoxyaniline (Ia) of Example I in Makrolon polycarbonate binder, and an inorganic photogenerating layer comprised of trigonal selenium, was prepared as follows:

A dispersion of trigonal selenium and poly(N-vinylcarbazole) was prepared by ball milling 1.6 grams of trigonal selenium and 1.6 grams of poly(N-vinylcarbazole) in 14 milliliters each of tetrahydrofuran and toluene. Ten (10) grams of the resulting slurry was then diluted with a solution of 0.25 gram of N,N-bis(4-biphenylyl)-3,5-dimethoxyaniline in 5 milliliters each of tetrahydrofuran and toluene. A 1.0 micron thick photogenerator layer was fabricated by coating the above dispersion onto an aluminized Mylar substrate, thickness of 50 microns, with a multiple-clearance film applicator, followed by drying in a forced air oven at 135° C. for 5 minutes. A solution for the hole transport layer was then prepared by dissolving 1.0 gram of N,N-bis(4-biphenylyl)-3,5-dimethoxyaniline and 1.0 gram of Makrolon polycarbonate in 12 milliliters of methylene chloride. This solution was then coated over the photogenerator layer by means of a multiple-clearance film appliator. The resulting member was subsequently dried in a forced air oven at 130° C. for 30 minutes resulting in an 25 micron thick transport layer.

The above fabricated imaging member was electrically tested by negatively charging it with a corona, and discharged by exposing to white light of wavelengths of from 400 to 700 nanometers. Charging was accomplished with a single wire corotron in which the wire was contained in a grounded aluminum channel and was strung between two insulating blocks. The acceptance potential of this imaging member after charging, and its residual potential after exposure were recorded. The procedure was repeated for different exposure energies supplied by a 75 watt Xenon arc lamp of incident radiation, and the exposure energy required to discharge the surface potential of the member to half of its original value was determined. This surface potential was measured using a wire loop probe contained in a shielded cylinder, and placed directly above the photoreceptor member surface. This loop was capacitively coupled to the photoreceptor surface so that the voltage of the wire loop corresponds to the surface potential. Also, the cylinder enclosing the wire loop was connected to the ground.

For this imaging member the acceptance potential was 1,000 volts, the residual potential was 35 volts, and the half decay exposure sensitivity was 3.0 egs/cm$^2$. Further, the electrical properties of this photoresponsive imaging member remained essentially unchanged for 1,000 cycles of repeated charging and discharging.

EXAMPLE V

A layered photoresponsive imaging member with a transport layer of N,N-bis(4-biphenylyl)-3,5-dimethoxyaniline of Example I in polycarbonate Z, and an amorphous selenium photogenerator layer was fabricated as follows:

A 0.5 micron thick layer of amorphous selenium on a ball grained aluminum plate of a thickness of 175 microns was prepared by conventional vacuum deposition techniques. Vacuum deposition was accomplished at a vacuum of $10^{-6}$ Torr, while the substrate was maintained at about 50° C. A hole transport layer on top of the amorphous selenium layer was obtained by coating a solution of 50 percent by weight each of N,N-bis(4-biphenylyl)-3,5-dimethoxyaniline and polycarbonate Z in methylene chloride using a multiple-clearance film applicator. This solution was prepared by dissolving 5 grams of N,N-bis(4-biphenylyl)-3,5-dimethoxyaniline and 5 grams of polycarbonate Z in 50 milliliters of methylene chloride. Thereafter, the resulting device was dried in a forced air oven at 50° C. for 1 hour to form a 30 microns thick transport layer. Subsequently, the imaging member was cooled to room temperature, followed by electrical testing in accordance with the procedure of Example IV using a 450 nanometers monochromatic light for irradiation. Specifically, this imaging member was negatively charged to 1,000 volts and discharged to a residual potential of 25 volts. The half decay exposure sensitivity for this device was 2.5 ergs/cm$^2$. The electrical performance of this imaging member remained essentially the same after 1,000 cycles of repeated charging and discharging.

EXAMPLE VI

A layered photoresponsive imaging member comprised of bis(4-ethoxycarbonyl-4'-biphenylyl)-4-biphenylylamine (IIa) of Example II in polycarbonate Z as the hole transport layer, and amorphous selenium as the photogenerator was fabricated as follows:

A 0.5 micron thick layer of amorphous selenium on a ball grained aluminum plate of a thickness of 175 microns was prepared in accordance with the procedure of Example V. A hole transport layer on top of the amorphous selenium layer was obtained by coating a solution of 50 percent by weight each of bis(4-ethoxycarbonyl-4'-biphenylyl)-4-biphenylylamine and polycarbonate Z in methylene chloride using a multiple-clearance film applicator. This solution was prepared by dissolving 5 grams of bis(4-ethoxycarbonyl-4'-biphenylyl)-4-biphenylylamine and 5 grams of polycarbonate Z in 50 milliliters of methylene chloride. Thereafter, the resulting device was dried in a forced air oven at 50° C. for 1 hour to form a 10 microns thick transport layer. Subsequently, the imaging member was cooled to room temperature, followed by electrical testing in accordance with the procedure of Example IV using a 450 manometers monochromatic light for irradiation. Specifically, this imaging member was negatively charged to 900 volts and discharged to a residual potential of 40 volts. The half decay exposure sensitivity for this device was 3.5 ergs/cm$^2$. The electrical performance of this imaging member remained essentially the same after 1,000 cycles of repeated charging and discharging.

EXAMPLE VII

A layered photoresponsive imaging member comprised of bis(4-ethoxycarbonyl-4'-biphenylyl)-4-biphenylylamine (IIa) of Example II in poly(methyl methacrylate) as the hole transport layer, and trigonal selenium as the photogenerator was fabricated as follows:

A 1.0 micron trigonal selenium photogenerator layer was prepared on an aluminized Mylar substrate by repeating the procedure of Example IV except that bis(4-ethoxycarbonyl-4'-biphenylyl)-4-biphenylylamine was used in place of N,N-bis(4-biphenylyl)-3,5-dimethoxyanilne. A solution for the transport layer was prepared by dissolving 0.7 gram of bis(4-ethoxycarbonyl-4'-biphenylyl)-4-biphenylylamine and 0.7 gram of poly(methyl methacrylate) in 8 milliliters of methylene chloride. This solution was coated on top of the trigonal selenium generator layer by means of a multiple-clearance film applicator. The resulting member was dried in a forced air oven at 130° C. for 30 minutes resulting in a dry thickness for the transport layer of 20 microns. Electrical testing was accomplished by repeating the procedure of Example IV. For this imaging member, the acceptance potential was 1,000 volts, and the half decay exposure sensitivity was 3.5 egs/cm$^2$.

EXAMPLE VIII

A layered photoresponsive device comprised of bis[4-(acetoxymethyl)-4'-biphenylyl]-4-biphenylylamine (IIb) of Example III in Merlon polycarbonate as the transport molecule, and amorphous selenium as the photogenerator, was fabricated as follows:

A 0.5 micron thick layer of amorphous selenium on a ball grained aluminum plate of a thickness of 125 microns was prepared by repeating the process of Example V. A hole transport layer on top of the amorphous selenium layer was obtained by coating a solution of 5 grams each of bis[4-(acetoxymethyl)-4'-biphenylyl]-4-biphenylylamine and Merlon polycarbonate in 40 milliliters of methylene chloride using a multiple-clearance film applicator. Thereafter, the resulting device or imaging member was dried in a forced air oven at 50° C. for 1 hour to form a 18 microns thick transport layer.

Electrical testing was affected by repeating the procedure of Example V, and substantially similar results were achieved.

EXAMPLE IX

A photoresponsive device comprised of bis[4-(acetoxymethyl)-4'-biphenylyl]-4-biphenylylamine (IIb) of Example III as the transporting molecule in polycarbonate Z, and squarylium pigments as the photogenerator was prepared as follows:

A ball grained aluminum substrate was coated with a solution of 1 milliliter of 3-aminopropyl trimethoxysilane in 100 milliliters of ethanol. The coating was heated at 110° C. for 10 minutes resulting in the formation of a 0.1 micron thick polysiloxane layer. A dispersion of a photogenerator prepared by ball milling a mixture of 0.075 gram of bis(N,N'-dimethylaminophenyl)squaraine and 0.13 gram polycarbonate Z in 12 milliliters of methylene chloride for 24 hours was then coated on top of the polysilane layer. After drying the coating in a forced air oven at 135° C. for 6 minutes, a 0.5 micron thick squarylium photogenerating layer was obtained.

A solution for the transport layer was then prepared by dissolving 1.0 gram each of bis[(4-(acetoxymethyl)-4'-biphenylyl]-4-biphenylylamine and polycarbonate Z in 15 milliliters of methylene chloride. This solution was then coated over the above photogenerator layer using a multiple clearance fil applicator. The resulting device was dried in a forced air oven at 135° C. for 30 minutes resulting in a 20 micron thick electon transport layer.

Electrical testing was affected by repeating the procedure of Example IV. Specifically, the device was charged negatively to 1,100 volts and discharged with 830 nanometers monochromatic light. For this imging device, the half decay exposure sensitivity was 3.5 ergs/cm$^2$.

EXAMPLE X

A photoresponsive imaging device with a spray coated transport layer comprised of bis[4-(acetoxymethyl)-4'-biphenylyl]-4-biphenylylamine (IIb) of Example III and a trigonal selenium photogenerator was fabricated as follows:

A 1 micron thick trigonal selenium photogenerator layer on an aluminized Mylar was prepared by repeating the procedure of Example IV using bis[4-(acetoxymethyl)-4'-biphenylyl]-4-biphenylylamine in place of N,N-bis(4-biphenylyl)-3,5-dimethoxyaniline. A solution for the transport layer was prepared by dissolving 2 grams each of bis[4-(acetoxymethyl)-4'-biphenylyl]-4-biphenylylamine and Makrolon polycarbonate in 30 millliters of methylene chloride. This solution was coated over the photogenerator layer using a multiple-clearace film applicator in accordance with the procedure as described in Example IV. The coating was dried in a forced air oven at 135° C. for 30 minutes yielding a transport layer of a thickness of 15 microns.

Electrical testing was affected by repeating the procedure of Example IV, and substantially similar results were achieved.

Although the invention has been described with reference to specific preferred embodiments, it is not intended to be limited thereto, rather those skilled in the art will recognize variations and modifications may be made therein which are within the spirit of the invention and within the scope of the following claims.

What is claimed is:

1. A photoconductive imaging member comprised of a supporting substrate, an inorganic photogenerating layer, or a photogenerating layer comprised of metal free phthalocyanines, metal phthalocyanines, vanadyl phthalocyanines, squaraines, perylenes, or dibromoanthanthrone; and a charge transport layer comprised of N,N-bis(biarylyl)aniline compounds of formula (I) or tris(biarylyl)amine compounds of Formula (II), wherein R, R', R" are independently selected from the group consisting of hydrogen, halogen, alkyl, aryl, alkoxy, and alkoxycarbonyl, and x, y, and z are the numbers 0, 1, or 2.

2. A photoconductive imaging member comprised of a supporting substrate; an inorganic photogenerating layer, and a charge transport layer comprised of N,N-bis(biarylyl)aniline compounds of Formula (I) wherein R, R', R" are independently selected from the group consisting of hydrogen, halogen, alkyl, aryl, alkoxy, and alkoxycarbonyl, and x, y, and z are the numbers 0, 1, or 2.

3. A photoconductive imaging member comprised of a suppoting substrate, an inorganic photogenerating layer, and a charge transport layer comprised of tris(biarylyl)amine compounds of Formula (II) where R, R', R" are independently selected from the group consisting of hydrogen, halogen, alkyl, aryl, alkoxy, and alkoxycarbonyl, and x, y, and z are the numbers 0, 1, or 2.

4. A photoconductive imaging member in accordance with claim 2 wherein alkyl contains from 1 to about 20 carbon atoms.

5. A photoconductive imaging member in accodance with claim 3 wherein alkyl contains from 1 to about 20 carbon atoms.

6. A photoconductive imaging member in accordance with claim 2 wherein alkyl is methyl.

7. A photoconductive imaging member in accordance with claim 3 wherein alkyl is methyl.

8. A photoconductive imaging member in accordance with claim 2 wherein alkoxy is methoxy.

9. A photoconductive imaging member in accordance with claim 3 wherein alkoxy is methoxy.

10. A photoconductive imaging member in accordance with claim 2 wherein the transport compound is N,N-bis(4-biphenylyl)-3,5-dimethoxyaniline (Ia); N,N-bis(4-biphenylyl)-3,5-dimethylaniline (Ib); N,N-bis(4-methyl-4'-biphenylyl)-3-methoxyaniline (Ic); N,N-bis(4-methyl-4'-biphenylyl)-3-chloroaniline (Id); or N,N-bis(4-bromo-4'-biphenylyl)-3,5-dimethoxyaniline (Ig).

11. A photoconductive imaging member in accordance with claim 3 wherein the transport compound is 4-biphenylyl bis(4-ethoxycarbonyl-4'-biphenylyl)amine (IIa); 4-biphenylyl bis(4-acetoxymethyl-4'-biphenylyl)amine (IIb); or 4-ethoxycarbonyl-4'-bisphenylyl bis(4-methyl-4'-biphenylyl)amine (IId).

12. A photoconductive imaging member in accordance with claim 2 wherein the photogenerating layer is comprised of inorganic photoconductive pigments.

13. A photoconductive imaging member in accordance with claim 3 wherein the photogenerating layer is comprised of inorganic photoconductive pigments.

14. A photoconductive imaging member in accordance with claim 2 wherein the photogenerating layer is a perylene, squaraine, metal free phthalocyanine, metal phthalocyanine, vanadyl phthalocyanine, or dibromoanthanthrone.

15. A photoconductive imaging member in accordance with claim 13 wherein the photogenerating layer is selenium, or selenium alloys.

16. A photoconductive imaging member in accordance with claim 12 wherein the photogenerating layer is trigonal selenium.

17. A photoconductive imaging member in accordance with claim 13 wherein the photogenerating layer is trigonal selenium.

18. An imaging member in accordance with claim 2 wherein the photogenerating layer is situated between the supporting substrate and the charge transport layer.

19. An imaging member in accordance with claim 3 wherein the photogenerating layer is situated between the supporting substrate and the charge transport layer.

20. An imaging member in accordance with claim 1 wherein the supporting substrate is aluminum, or an organic polymeric composition.

21. An imaging member in accordance with claim 2 wherein the supporting substrate is aluminum, or an organic polymeric composition.

22. An imaging member in accordance with claim 3 wherein the supporting substrate is aluminum, or an organic polymeric composition.

23. An aging member in accordance with claim 1 wherein the photogenerating, or the charge transport compounds are dispersed in a resinous binder.

24. An imaging member in accordance with claim 2 wherein the photogenerating, or the charge transport compounds are dispersed in a resinous binder.

25. An imaging member in accordance with claim 3 wherein the photogenerating, or the charge transport compounds are dispersed in a resinous binder.

26. An imaging member in accordance with claim 23 wherein the resinous binder is a polyester, poly(vinyl butyral), polycarbonate, or poly(vinyl formal).

27. An imaging member in accordance with claim 1 containing a hole blocking layer and an adhesive layer.

28. An imaging member in accordance with claim 2 containing a hole blocking layer and an adhesive layer.

29. An imaging member in accordance with claim 3 containing a hole blocking layer and an adhesive layer.

30. An imaging member in accordance with claim 1 containing a hole blocking layer or an adhesive layer.

31. An imaging member in accordance with claim 2 containing a hole blocking layer or an adhesive layer.

32. An imaging member in accordance with claim 3 containing a hole blocking layer or an adhesive layer.

33. A method of imaging which comprises generating an electrostatic image on the imaging member of claim 1, subsequently transferring this image to a suitable substrate, and thereafter permanently affixing the image thereto.

34. A method of imaging which comprises generating an electrostatic image on the imaging member of claim 2, subsequently transferring this image to a suitable substrate, and thereafter permanently affixing the image thereto.

35. A method of imaging which comprises generating an electrostatic image on the imaging member of claim 3, subsequently transferring this image to a suitable substrate, and thereafter permanently affixing the image thereto.

36. A method of imaging in accordance with claim 33 wherein the transport molecules are N,N-bis(4-biphenylyl)-3,5-dimethoxyaniline (Ia); N,N-bis(4-biphenyllyl)-3,5-dimethylaniline (Ib); N,N-bis(4-methyl-4'-biphenylyl)-3-methoxyaniline (Ic); N,N-bis(4-methyl-4'-biphenylyl)-3-chloroaniline (Id); N,N-bis(4-bromo-4'-biphenylyl)-3,5-dimethoxyaniline (Ig); 4-biphenylyl bis(4-ethoxycarbonyl-4'-biphenylyl)amine (IIa); 4-biphenylyl bis(4-acetoxymethyl-4'-biphenylyl)amine (IIb); or 4-ethoxycarbonyl-4'-biphenylyl bis(4-methyl-4'-biphenylyl)amine (IId).

37. A method of imaging in accordance with claim 34 wherein the transport molecules are N,N-bis(4-biphenylyl)-3,5-dimethoxyaniline (Ia); N,N-bis(4-biphenylyl)-3,5-dimethylaniline (Ib); N,N-bis(4-methyl-4'-biphenylyl)-3-methoxyaniline (Ic); N,N-bis(4-methyl-4'-biphenylyl)-3-chloroaniline (Id); or N,N-bis(4-bromo-4'-biphenylyl)-3,5-dimethoxyaniline (Ig).

38. A method of imaging in accordance with claim 36 wherein the transport molecules are 4-biphenylyl bis(4-ethoxycarbonyl-4'-biphenylyl)amine (IIa); 4- biphenylyl bis(4-acetoxymethyl-4'-biphenylyl)amine (IIb); or 4-ethoxycarbonyl-4'-biphenylyl bis(4-methyl-4'-biphenylyl)amine (IId).

39. An imaging member in accordance with claim 1 wherein the photogenerating layer is comprised of trigonal selenium.

40. An imaging member in accordance with claim 1 wherein the photosensitivity thereof is from about 400 to about 700 nanometers.

41. A photoconductive imaging member comprised of an inorganic photogenerating layer, or a photogenerating layer comprised of metal free phthalocyanines, metal phthalocyanines, vanadyl phthalocyanines, squaraines, perylenes, or dibromoanthanthrone; and a charge transport layer comprised of N,N-bis(biarylyl)aniline compounds of Formula (I) or tris(biarylyl)amine compounds of Formula (II), wherein R, R', R" are independently selected from the group consisting of hydrogen, halogen, alkyl, aryl, alkoxy, and alkoxycarbonyl, and x, y, and z are the numbers 0, 1, or 2.

42. A photoconductive imaging member comprised of an inorganic photogenerating layer, and a charge transport layer comprised of N,N-bis(biarylyl)aniline compounds of Formula (I) or tris(biarylyl)amine compounds of Formula (II), wherein R, R', R" are independently selected from the group consisting of hydrogen, halogen, alkyl, aryl, alkoxy, and alkoxycarbonyl, and x, y, and z are the numbers 0, 1 or 2.

43. A photoconductive imaging member comprised of a an inorganic photogenerating layer, and a charge transport layer comprised of N,N-bis(biarylyl)aniline compounds of Formula (I) wherein R, R', R" are independently selected from the group consisting of hydrogen, halogen, alkyl, aryl, alkoxy, and alkoxycarbonyl, and x, y, and z are the numbers 1 or 2.

44. A photoconductive imaging member comprised of an inorganic photogenerating layer, and a charge transport layer comprised of tris(biarylyl)amine compounds of Formula (II) wherein R, R', R" are independently selected from the group consisting of hydrogen, halogen, alkyl, aryl, alkoxy, and alkoxycarbonyl, and x, y, and z are the numbers 1 or 2.

* * * * *